US009861537B2

(12) United States Patent
Louwrens

(10) Patent No.: US 9,861,537 B2
(45) Date of Patent: Jan. 9, 2018

(54) GOWN SYSTEM

(71) Applicant: Neil Andrew Louwrens, Redding, CA (US)

(72) Inventor: Neil Andrew Louwrens, Redding, CA (US)

( * ) Notice: Subject to any disclaimer, the term of this patent is extended or adjusted under 35 U.S.C. 154(b) by 0 days.

(21) Appl. No.: 15/467,242

(22) Filed: Mar. 23, 2017

(65) Prior Publication Data

US 2017/0281431 A1 Oct. 5, 2017

Related U.S. Application Data

(60) Provisional application No. 62/316,983, filed on Apr. 1, 2016.

(51) Int. Cl.

| | |
|---|---|
| ***B65D 85/18*** | (2006.01) |
| ***A61F 15/00*** | (2006.01) |
| ***A41D 13/12*** | (2006.01) |
| ***B65D 83/08*** | (2006.01) |
| ***B65D 25/22*** | (2006.01) |

(52) U.S. Cl.

CPC ............ *A61F 15/001* (2013.01); *A41D 13/12* (2013.01); *B65D 25/22* (2013.01); *B65D 83/0805* (2013.01); *B65D 85/18* (2013.01)

(58) Field of Classification Search

CPC ................................. A41D 13/12; A47F 1/08
USPC .......................................... 221/203; 493/405
See application file for complete search history.

(56) References Cited

U.S. PATENT DOCUMENTS

| | | | | |
|---|---|---|---|---|
| 5,622,281 A * | 4/1997 | Annand | A47K 10/24 | 206/494 |
| 2005/0199690 A1* | 9/2005 | Peterson | B65D 5/0254 | 229/122.1 |
| 2013/0105511 A1* | 5/2013 | Graneto, III | A47F 1/08 | 221/303 |
| 2013/0318682 A1* | 12/2013 | Graneto, III | A41D 13/1236 | 2/114 |

* cited by examiner

*Primary Examiner* — Timothy Waggoner
*Assistant Examiner* — Ayodeji Ojofeitimi
(74) *Attorney, Agent, or Firm* — Donald R. Boys; Central Coast Patent Agency, Inc.

(57) ABSTRACT

A gown dispenser system has a plurality of hospital gowns, each having a back region, the gowns folded and stacked back region facing up, such that, pulling on the back region of a gown on top of the stack removes that gown from the stack and exposes the back region of the next gown in the stack, an enclosure containing the stack of gowns, the enclosure having an opening exposing the back region of the gown at the top of the stack, enabling a user to grasp the exposed back region and pull the topmost gown from the enclosure, exposing the next gown in the stack, and an interface mechanism attached to the enclosure, enabling the enclosure to be suspended on a substantially vertical surface, with the opening facing outward from the substantially vertical surface. Gowns are drawn from the enclosure one-at-a-time, at need.

9 Claims, 6 Drawing Sheets

GOWN SYSTEM

CROSS-REFERENCE TO RELATED DOCUMENTS

The present patent application claims priority to provisional application 62/316,983, filed on Apr. 1, 2016, entitled, "Gown System". Disclosure of the priority applications is incorporated herein in its entirety by reference.

BACKGROUND OF THE INVENTION

1. Field of the Invention

The invention is in the technical area of dispensing items, such as garments, and has particular application in sanitation in medical practice, and pertains in one embodiment more particularly to providing hospital gowns to medical staff.

2. Description of Related Art

In many technical arts, disposable items are provided for temporary use. Many example may be listed, such as gloves in both medical and food arts, aprons in food arts, and sanitary gowns in medical environments. Medical practice is a particular, but not a limiting focus, for applications of the instant invention, and is used exemplary below to describe specific examples as embodiments of the present invention.

It is often necessary in medical practice for a physician, nurse or other medical practitioner to quickly don a hospital gown before entering a sanitary area. The present invention provides a quick and practical solution to this need.

BRIEF SUMMARY OF THE INVENTION

In one exemplary embodiment of the invention, a gown dispenser system is provided, comprising a plurality of sterile hospital gowns, each having a back region, the gowns folded and stacked back region facing up, such that, pulling on the back region of a gown on top of the stack removes that gown from the stack and exposes the back region of the next gown in the stack, an enclosure containing the stack of gowns, the enclosure having an opening in one surface exposing the back region of the gown at the top of the stack, enabling a user to grasp the exposed back region and pull the topmost gown from the enclosure, exposing the next gown in the stack, and an interface mechanism attached to the enclosure, enabling the enclosure to be suspended on a substantially vertical surface, with the opening facing outward from the substantially vertical surface. Gowns are drawn from the enclosure one-at-a-time, at need.

In one embodiment, a pull tab is attached to the back region of each gown in the stack, providing an appendage to be grasped to pull a gown from the enclosure. Also in one embodiment of the system, the enclosure is implemented in paperboard, with a portion of the paperboard on the one surface of the enclosure perforated in a shape to provide the opening, with the paperboard within the perforated region removed. Also in one embodiment, the interface mechanism comprises one or more brackets attached to a side of the container opposite the side perforated for the opening, the brackets configured to enable hanging the container from a top edge of a door. In one embodiment, each gown, unfolded, comprises an upper portion having a front region and the back region, a left and a right sleeve, each of a length to cover an arm of a person, and an upper head opening, the back region extending to a lower extremity of the left and right sleeves, and a front apron portion, having a width from the left to the right sleeve, extending downward from the upper portion for a height to cover a major portion of a person's body below the extension of the left and right sleeves. In one embodiment, the front portion has tie extensions extending horizontally from opposite edges of the front portion, at a height for tying the front portion of the gown around the body of a user. And in one embodiment the gowns are folded by folding the left and right sleeves to the front along edges of the front portion, and a lower part of the front portion upward to the front along a substantially horizontal line, leaving the tab free at the back of the upper portion of the folded gown.

In another aspect of the invention, a method for providing a sterile gown to a user from a gown-dispensing system is provided, comprising folding a plurality of sterile gowns having a back region of each gown in a stack with the back region facing up, and placing the gowns in an enclosure having a front and a back surface, the back surface having an opening exposing the back region of the top-most gown on the stack, supporting the enclosure on a substantially vertical surface by an interface mechanism with the opening in the back surface facing away from the substantially vertical surface, grasping the back region by a user and pulling a topmost gown out through the opening in the back surface, leaving a next gown in the stack having the pull tab exposed through the opening, and donning the gown. In one embodiment of the method a pull tab is attached to the back region of each gown in the stack, and the pull tab is grasped to pull a gown from the enclosure.

In one embodiment of the method, each gown in the stack has an upper portion having a front region and the back region, a left and a right sleeve, each of a length to cover an arm of a person, and an upper head opening, the back region extending to a lower extremity of the left and right sleeves, a front apron portion, having a width from the left to the right sleeve, extending downward from the upper portion for a height to cover a major portion of a person's body below the extension of the left and right sleeves, and the gowns are folded by folding the left and right sleeves to the front along edges of the front portion, and folding a lower part of the front portion upward to the front along a substantially horizontal line, leaving the back region free at the back of the upper portion of the folded gown, and the method further comprises the user pulling the upper portion over the user's head and placing the head through the upper head opening, and the user stepping back away from the enclosure, pulling the balance of the sterile gown from the enclosure.

DETAILED DESCRIPTION OF THE INVENTION

Figure 1A:
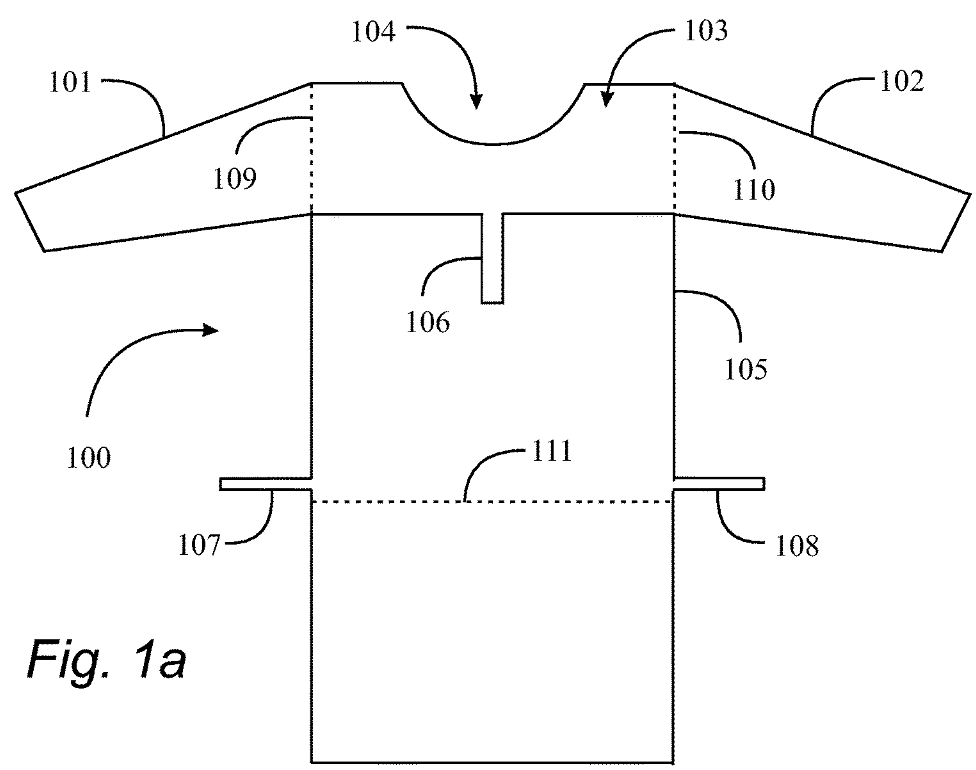
FIG. 1*a* is an illustration of a hospital gown in an embodiment of the invention.

FIG. 1*a* is an illustration of a hospital gown 100 in an embodiment of the invention. In this view the gown is fully deployed (not folded) and is viewed from the back of the gown. Gown 100 has a contiguous upper portion 103 that applies over a user's shoulders, with an opening 104 for the user's head, and has a left arm portion 101 and a right arm portion 102. It will be apparent to the skilled person that, as shown in FIG. 1, upper portion 103 and arm portions 101 and 102 have two layers, to fit over the shoulders, front and back, and to cover the arms when the gown is worn.

Upper portion 103 has an extension 106, extending from the layer of portion 103 to the back of the gown, which serves as a pull-tab in deploying the gown for use, as is described in enabling detail below. A single layer lower portion 105 extends below the upper portion to a lowermost extremity, and is contiguous with the front of upper portion 103. If one were to grasp tab 106 and pull in the direction out of the figure, upper portion 103 would open, presenting opening 104 for the user's head, and the gown could be donned by pulling upper portion 103 over the head, and down so the user's head passes through opening 104, which would leave lower portion 105 to the user's front.

Gown 100 further comprises two extensions as tie-tabs 107 and 108, laterally to each side in FIG. 1*a*. These tie-tabs act as ties once the user dons the gown, to tie lower portion 105 around the user's torso. Further, FIG. 1*a* illustrates fold lines 109, 110, and 111, which are lines along which the gown may be folded to be placed in a dispenser in an embodiment of the invention described in enabling detail below.

Figure 1B:
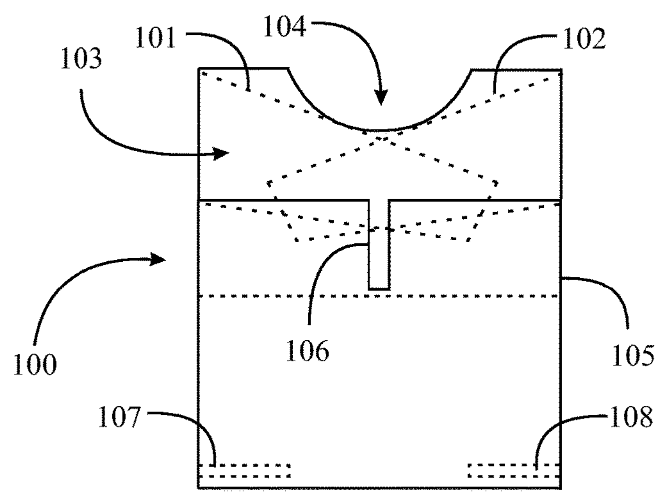
FIG. 1*b* is an illustration of the gown of FIG. 1*a* folded.

FIG. 1*b* is an illustration of gown 100 of FIG. 1*a* folded along fold lines 109, 110 and 111. Each of tie-tabs 107 and 108 has a fold line at the edge of lower portion 105, but these fold lines are not shown in FIG. 1*a*. Sleeves 101 and 102 are folded along fold lines 109 and 110 respectively, to the front (into the plane of the figure), to lie against the front of the gown as shown in FIG. 1*b*. Tie-abs 107 and 108 are also folded to the front to lie against the front of the gown. Lastly the portion of the gown below fold line 111 is also folded up to the front along fold line 111, to lie against the front of the gown. After these operations, the folded gown is as seen in FIG. 1*b*.

In alternative embodiments, the tie-tabs might be in different positions on a gown, and in one embodiment two tie-tabs may be joined to the gown on the same side. The position, length, and use of the tie-tabs in ties on a gown after the gown is donned is related to specific practice in particular circumstances, and the tie-tabs are not limiting in their position, length and the like.

Figure 2:
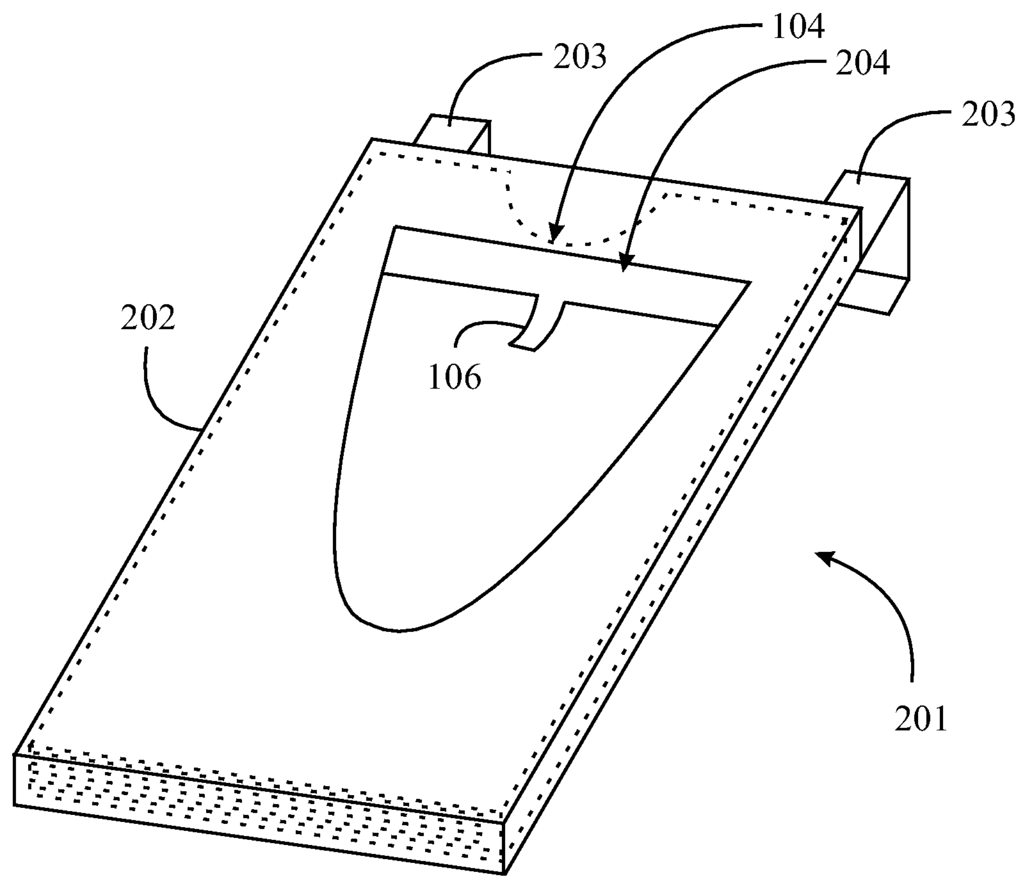
FIG. 2 is an illustration of a dispenser for providing folded gowns one-at-a-time to users.

FIG. 2 is an illustration of a dispenser 201 for providing folded gowns one-at-a-time to users. Dispenser 201 comprises a container 202 with one or more interfaces 203 for suspending the container from a vertical surface, such as a wall or a doorway. A plurality of folded gowns, folded according to FIG. 1*b* in one embodiment, is enclosed in a stack in container 202. Container 202 has an opening 204 on one major surface for allowing gowns to be presented to users, and for gowns to be withdrawn and donned by users.

It is emphasized that mounting on a vertical surface, such as a wall or a doorway, is a convenience and an option, not a limitation in the invention. In some cases, a dispenser may be mounted to a chair back, simply placed on a table or other supporting surface, or provided in many other ways. The important issue is that a user must be able to access a gown from the dispenser and don the gown in a sanitary fashion.

A stack of folded gowns within container 202 is positioned such that, when opening 204 is provided, in a manner described below, tab 106 of a topmost gown in the stack is presented, and is physically accessible to a user, such that the user may grasp the tab and pull, to at least partially dispense the connected gown from the container. The neck opening 104 of the topmost folded gown in the stack of gowns in container 202 is seen in dotted outline in FIG. 2.

In some embodiments of the invention it is important to certain persons to know when there is a limited number of gowns left in the dispenser. For this purpose, in one embodiment, the last few gowns in a dispenser container, for example the last five, may have a specific indicator, like a red dot, or other visible indicia, so users know there are only a limited supply left. In one embodiment radio-frequency identification (RFID) may be used to track the number of gowns in a container, and to alert when the number falls to a critical number. In this method, electronically-discoverable tags are attached, one to each gown. RFID uses electromagnetic fields to automatically identify and track the tags attached to gowns. The tags contain electronically stored information. Passive tags collect energy from a nearby RFID reader's interrogating radio waves. In such an embodiment, the RFID reader may be a part of the container, or placed near the container, and may have a transmitter to send an alert to an external device, which may be as simple as a cell phone of a person responsible for being sure gowns are available.

Container 202 may be constructed of a variety of materials, such as plastic, but in one embodiment a preferred material is paperboard of a thickness and strength to maintain its shape when handled, and when hung on a door or a wall. In various embodiments opening 204 may be shaped differently than shown in FIG. 2, and some shapes may facilitate feeding of individual gowns from the container. In addition, interfaces 203 may be provided in a variety of ways.

In one embodiment, wherein container 202 is constructed of paperboard, opening 204 is closed, but the outline seen in FIG. 2 is perforated in the material of the container, such that a user may remove the covering over the opening, presenting gowns accessible through the opening.

In an alternative embodiment, a separate outside container or support structure may be provided, made of more rigid material, like plastic or metal, and may be structured for a paperboard or other container of gowns to be placed in the outside container.

In the circumstance of a paperboard container, the container itself may be throwaway, so when the last gown is withdrawn, the container is just discarded, and a new container full of gowns is placed for service. In another embodiment, gowns may be replaceable in pre-stacked groups, perhaps in a sanitary covering that may be removed. In this circumstance container 202 may be of more sturdy construction, and may have a side opening that may be opened to allow a new stack of gowns to be inserted for use. In this circumstance the container may be designed to be cleanable, to be kept in sanitary condition. In some cases, the opening for a new stack of gowns may be in the top or bottom edge, or anywhere else, such that the stack of gowns may be inserted.

Figure 3:
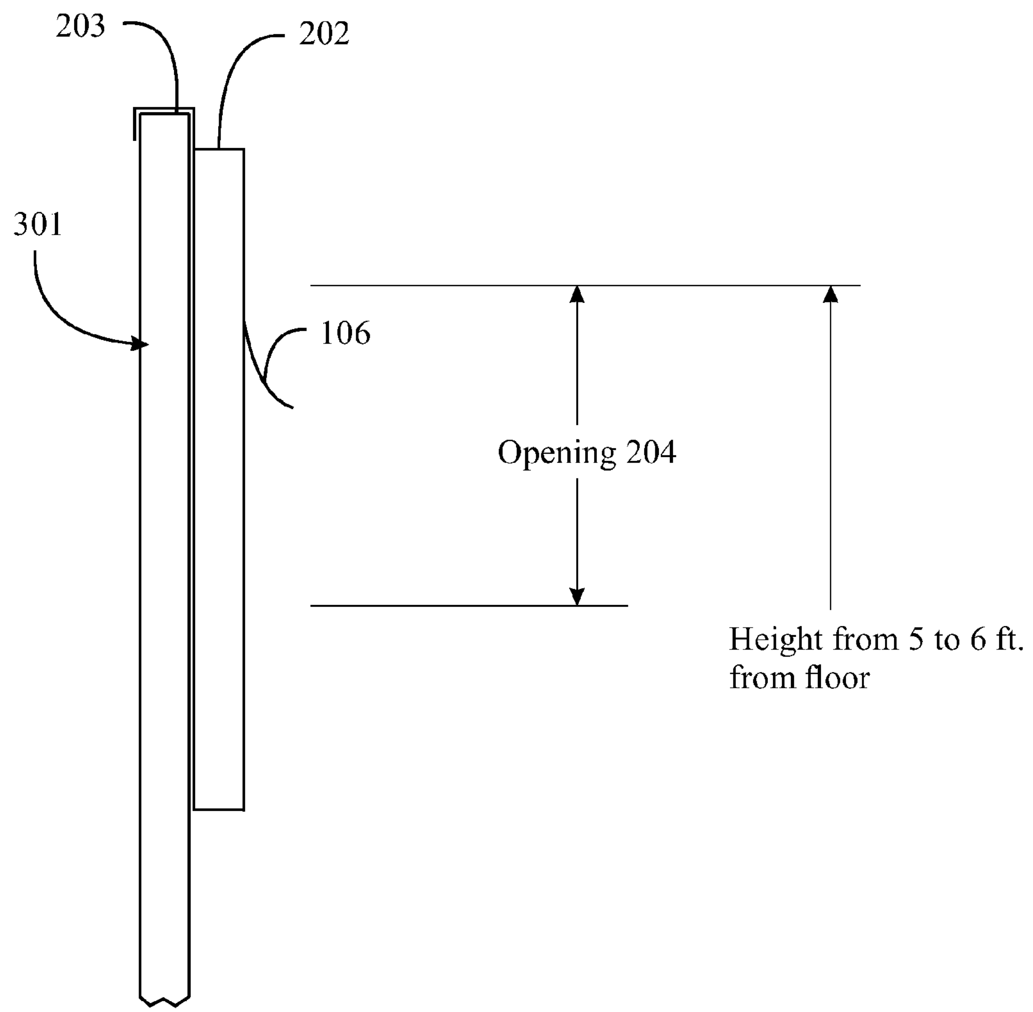
FIG. 3 is an illustration of the dispenser of FIG. 2 hung on a door.

FIG. 3 illustrates container 202 suspended on a door 301 by interfaces 203 engaging the top of the door. Opening 204 faces outward, away from door 301, positioned at a height between 5 and 6 feet in one embodiment. Opening 204 height is shown, and tab 106 may be seen extending out from opening 204, such that a user may easily grab and pull on the tab.

Figure 4A:
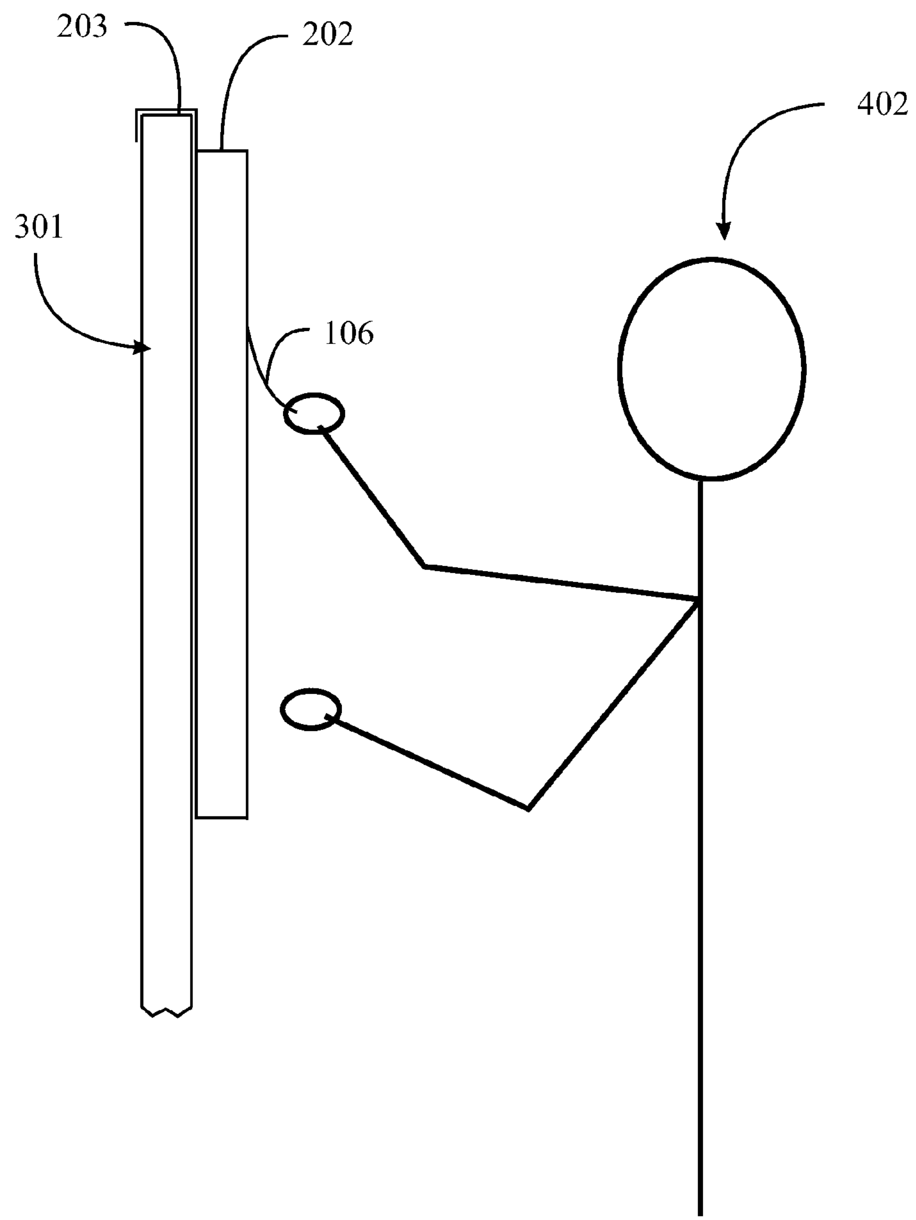
FIG. 4*a* is an illustration showing a person about to draw a gown from the dispenser of FIG. 3.

FIG. 4*a* illustrates a user 402, who may be a doctor or nurse, for example, reaching for and grasping tab 106 of a topmost gown in container 202 hung on door 301. In this example, it may be assumed that the door is entry to a hospital room or an operating theatre where a gown may be mandatory.

Figure 4B:
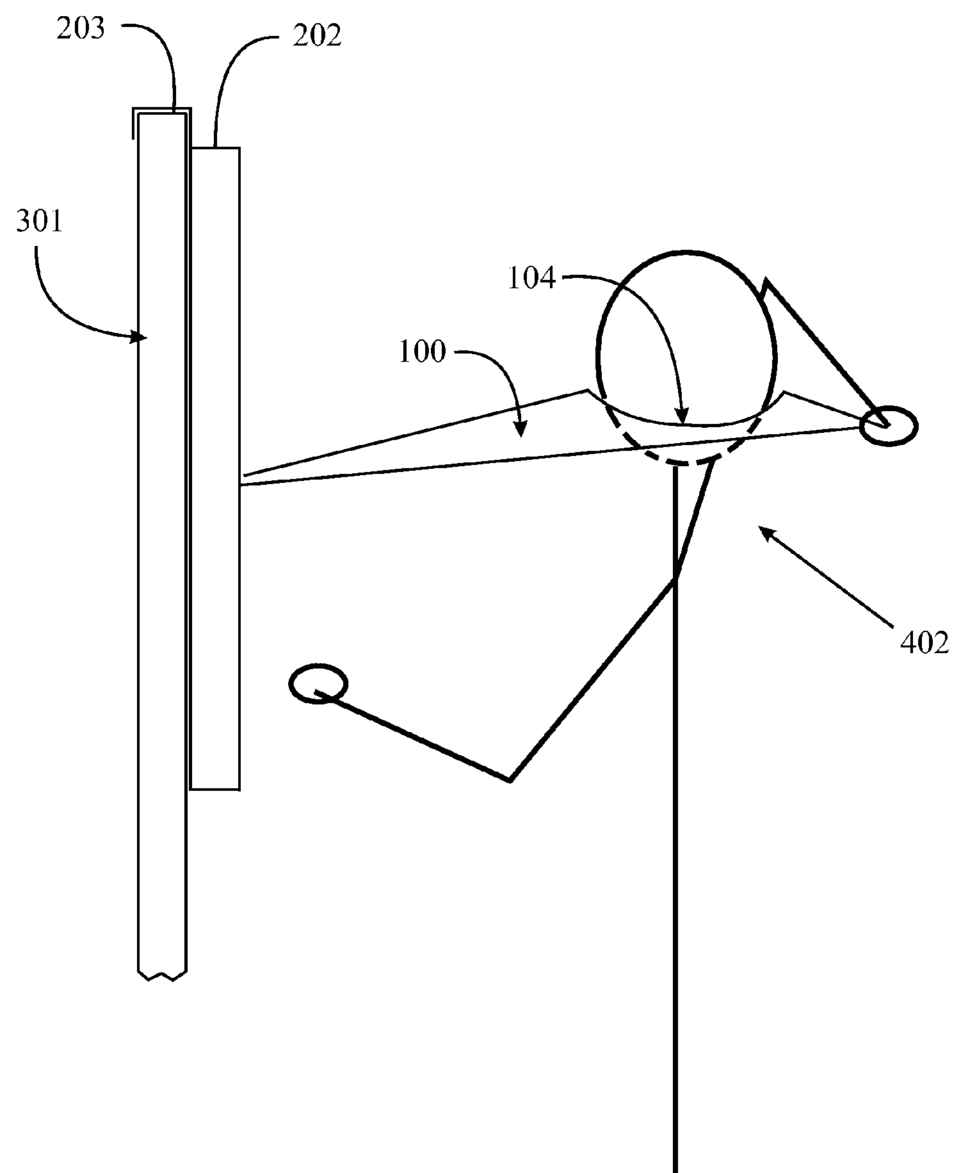
FIG. 4*b* is an illustration illustrating a second step in withdrawing a gown from the dispenser.

FIG. 4*b* illustrates user 402, having pulled a gown 100 partly from container 202, and having pulled the gown over his/her head, with the head now projected upward through opening 104 at the top of the upper portion of the gown. The folding of gown 100 and placement into container 202 presents the tab 106 at a convenient height for the user to grasp the tab and pull the gown, and the placement of the gown with back facing outward allows the step of pulling the gown over the user's head.

Figure 4C:
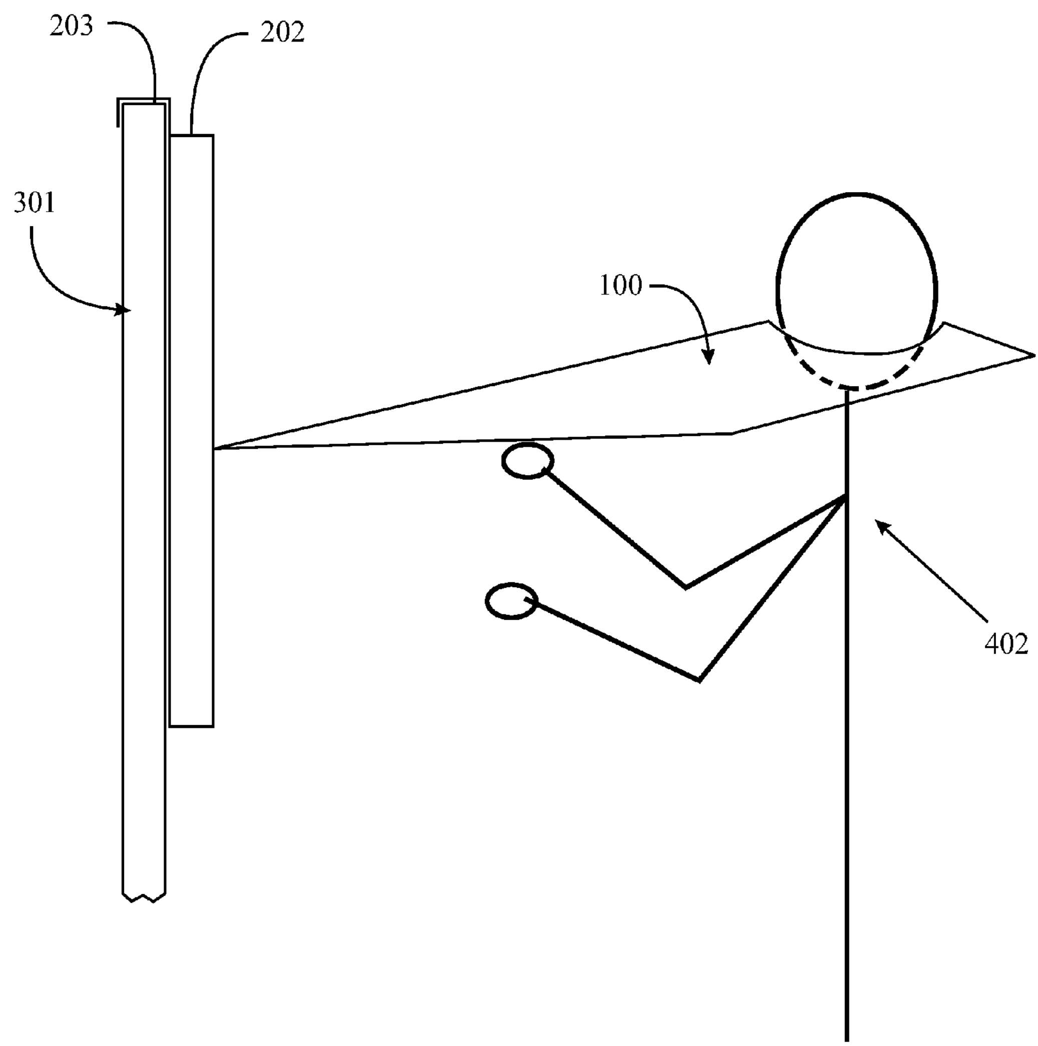
FIG. 4*c* is an illustration of a third step in withdrawing a gown from the dispenser.

FIG. 4*c* illustrates a third step, wherein the user, with his or her head through opening 104 of the gown, releases the gown with the hand that grasped the tab, and simply steps backward one or two steps, away from the dispenser, which action causes gown 100 to fully draw out of the dispenser. At this point the front of the gown may fall down in front of the user, and the user may easily put his/her arms into the sleeves of the gown, and then tie the gown around the torso. This final step is not shown, but will be fully apparent to the skilled person.

In one embodiment, the dispenser, including container 102, and gowns in or to be placed into the container, are provided fully sterilized, and protected in sterile form, into a sterile environment, such as an operating theatre. In yet another embodiment gowns in this invention may have a tie tab from one gown physically connected to a portion of a next gown in a stack. This version is useful in a procedure for donning gowns, that may be used in a sterile environment to prevent contamination in the process of donning a gown.

It is emphasized as well that gowns, to be compatible with aspects of this invention, need not be exactly the form and folding shown in FIGS. 1*a* and 1*b*, but may be made in some cases considerably differently. In one embodiment gowns provided for use in aspects of this invention have thumb holes in the ends of the sleeves, in a position that a wearer can pass his or her thumb through this opening, beforehand coverings are applied, which prevents the arms of the gown from riding up when the wearer is busy in performing tasks.

It will also be apparent to the skilled person that the embodiment described above with regard to FIGS. 1-4*c* is an example, and not limiting. The examples provided above are just that, examples, exemplary of specific implementations of the invention, and not limiting. The invention has application far beyond provision of sterile gowns in a hospital setting. Further, the gowns may be plastic or fabric of many sorts, and may be designed and implemented in a variety of ways, and also folded in a variety of ways. There are many alterations to the gown, the container, the openings, and the placement of the dispenser on a vertical surface that will fall within the scope of the invention. In some embodiments, the interfaces to the vertical surface may vary, both in form and number. In some embodiments, the opening in the container to present a gown for withdrawal may be different in shape and size. There are many options within the scope of the invention.

What is claimed is:

1. A gown dispenser system, comprising:

a plurality of sterile hospital gowns, each gown, unfolded, having an upper portion having a front region and the back region, a left and a right sleeve, each having an arm opening into the upper portion, of a length to cover an arm of a person, and an upper head opening, the back region extending down to a lower extremity of the arm openings into the upper portion, and a front apron portion having a width from the left to the right sleeve, extending downward from the upper portion for a height to cover a major portion of a person's body, the gowns folded and stacked with the back region facing up, such that, grasping and pulling on the back region of a gown on top of the stack removes that gown from the stack and exposes the back region of the next gown in the stack;

an enclosure containing the stack of gowns with the back regions facing up, the enclosure having an opening in one surface exposing the back region of the gown at the top of the stack, enabling a user to grasp the exposed back region, and to pull the topmost gown from the enclosure, exposing the next gown in the stack; and an interface mechanism attached to the enclosure, enabling the enclosure to be suspended on a substantially vertical surface, with the opening facing outward from the substantially vertical surface;

wherein gowns are drawn from the enclosure one-at-a-time, at need.

2. The gown-dispenser system of claim 1, wherein a pull tab is attached to the back region of each gown in the stack, providing an appendage to be grasped to pull a gown from the enclosure.

3. The gown-dispenser system of claim 1 wherein the enclosure is implemented in paperboard, with a portion of the paperboard on the one surface of the enclosure perforated in a shape to provide the opening, with the paperboard within the perforated region removed.

4. The gown-dispenser system of claim 1 wherein the interface mechanism comprises one or more brackets attached to a side of the container opposite the side perforated for the opening, the brackets configured to enable hanging the container from a top edge of a door.

5. The gown-dispenser system of claim 4 wherein the front portion has tie extensions extending horizontally from opposite edges of the front portion, at a height for tying the front portion of the gown around the body of a user.

6. The gown-dispenser system of claim 1 wherein the gowns are folded by folding the left and right sleeves to the front along edges of the front portion, and a lower part of the front portion upward to the front along a substantially horizontal line, leaving the back region free at the back of the upper portion of the folded gown.

7. A method for providing a sterile gown to a user from a gown-dispensing system, comprising:

folding a plurality of sterile gowns into a stack of gowns, each gown, unfolded, having an upper portion having a front region and the back region, a left and a right sleeve, each having an arm opening into the upper portion, of a length to cover an arm of a person, and an upper head opening, the back region extending down to a lower extremity of the arm openings into the upper portion, and a front apron portion having a width from the left to the right sleeve, extending downward from the upper portion for a height to cover a major portion of a person's body, a back region of each gown in the stack facing up, and placing the stack of gowns in an enclosure having a front and a back surface, the back surface having an opening exposing the back region of the top-most gown on the stack;

supporting the enclosure on a substantially vertical surface by an interface mechanism with the opening in the back surface facing away from the substantially vertical surface;

grasping the back region by a user and pulling a topmost gown out through the opening in the back surface, leaving a next gown in the stack having the back region exposed through the opening; and donning the gown.

8. The method of claim 7, wherein a pull tab is attached to the back region of each gown in the stack, and wherein the pull tab is grasped to pull a gown from the enclosure.

9. The method of claim 7 wherein each gown in the stack has an upper portion having a front region and the back region, a left and a right sleeve, each of a length to cover an arm of a person, and an upper head opening, the back region extending to a lower extremity of the left and right sleeves, a front apron portion, having a width from the left to the right sleeve, extending downward from the upper portion for a height to cover a major portion of a person's body below the extension of the left and right sleeves, and the gowns are folded by folding the left and right sleeves to the front along edges of the front portion, and folding a lower part of the front portion upward to the front along a substantially horizontal line, leaving the back region free at the back of the upper portion of the folded gown, further comprising:

the user pulling the upper portion over the user's head and placing the head through the upper head opening; and the user stepping back away from the enclosure, pulling the balance of the sterile gown from the enclosure.

* * * * *